United States Patent
McAdams et al.

(10) Patent No.: US 8,634,895 B2
(45) Date of Patent: Jan. 21, 2014

(54) BIOMEDICAL SURFACE ELECTRODE

(75) Inventors: Eric Thomas McAdams, Whitehead (GB); John McCune Anderson, Holywood (GB); James Andrew McLaughlin, Belfast (GB)

(73) Assignee: Intelesens Limited, Belfast (GB)

( * ) Notice: Subject to any disclaimer, the term of this patent is extended or adjusted under 35 U.S.C. 154(b) by 869 days.

(21) Appl. No.: 12/280,518

(22) PCT Filed: Feb. 16, 2007

(86) PCT No.: PCT/EP2007/001365
§ 371 (c)(1), (2), (4) Date: Aug. 22, 2008

(87) PCT Pub. No.: WO2007/096096
PCT Pub. Date: Aug. 30, 2007

(65) Prior Publication Data
US 2009/0043185 A1    Feb. 12, 2009

(30) Foreign Application Priority Data
Feb. 23, 2006   (IE) .................... S2006/0134

(51) Int. Cl.
*A61B 5/04* (2006.01)
*A61N 1/04* (2006.01)

(52) U.S. Cl.
USPC ............ 600/391; 600/392; 607/152; 607/153

(58) Field of Classification Search
USPC .................... 600/391, 392; 607/149, 152, 153
See application file for complete search history.

(56) References Cited

U.S. PATENT DOCUMENTS

| 4,422,461 A * | 12/1983 | Glumac .................... 607/152 |
| 4,736,752 A * | 4/1988 | Munck et al. ............. 607/152 |
| 4,852,571 A | 8/1989 | Gadsby et al. |
| 5,337,748 A * | 8/1994 | McAdams et al. .......... 600/396 |
| 5,354,328 A * | 10/1994 | Doan et al. ................. 607/129 |
| 6,019,877 A * | 2/2000 | Dupelle et al. ........... 204/196.11 |
| 6,356,779 B1 * | 3/2002 | Katzenmaier et al. ........ 600/391 |
| 6,731,977 B2 * | 5/2004 | Beck ............................ 604/20 |
| 7,403,807 B2 * | 7/2008 | Dupelle et al. ............ 600/372 |
| 2002/0099320 A1 | 7/2002 | Beck |
| 2004/0122500 A1 * | 6/2004 | Rouns ........................ 607/129 |
| 2006/0025665 A1 | 2/2006 | Dupelle et al. |

FOREIGN PATENT DOCUMENTS

EP   1 021 986 A2   7/2000

OTHER PUBLICATIONS

International Preliminary Report on Patentability issued Aug. 26, 2008 in PCT Application No. PCT/EP2007/001365.
International Search Report issued Oct. 17, 2007 in PCT Application No. PCT/EP2007/001365.
Written Opinion issued in PCT Application No. PCT/EP2007/001365.

* cited by examiner

*Primary Examiner* — Lee S Cohen
(74) *Attorney, Agent, or Firm* — Foley & Lardner LLP; Christopher J. McKenna; Paul M. H. Pua

(57) ABSTRACT

A flexible biomedical surface electrode comprises an insulating substrate (10), a conductive electrode layer (12) screen-printed on the substrate, and an insulating masking layer (14) on the electrode layer. The masking layer is configured to expose selected regions (16) of the electrode layer. An electrically conductive adhesive gel layer (18) on the masking layer makes electrical contact with the exposed regions of the electrode layer.

14 Claims, 2 Drawing Sheets

Figure 1:
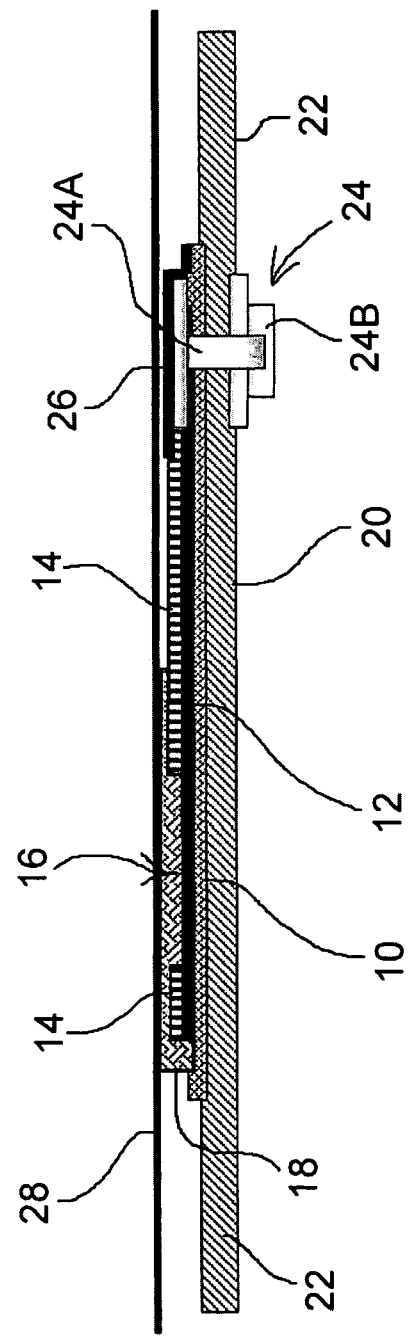
Figure 2:
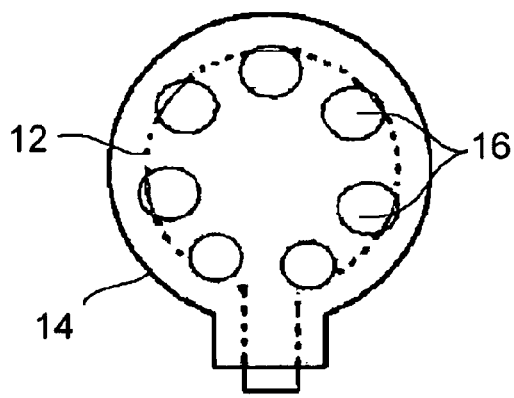
Figure 2:
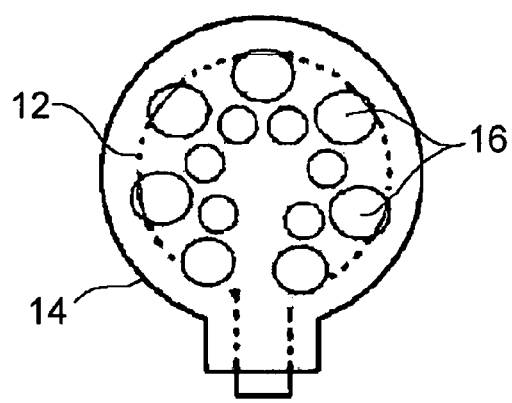
Figure 2:
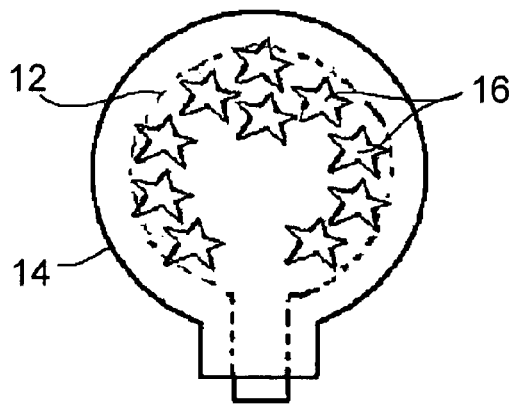
Figure 2:
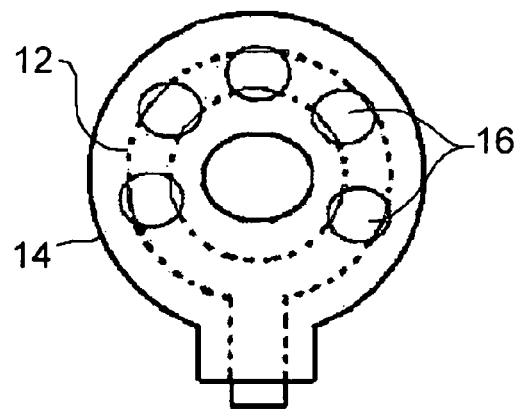
Figure 2:
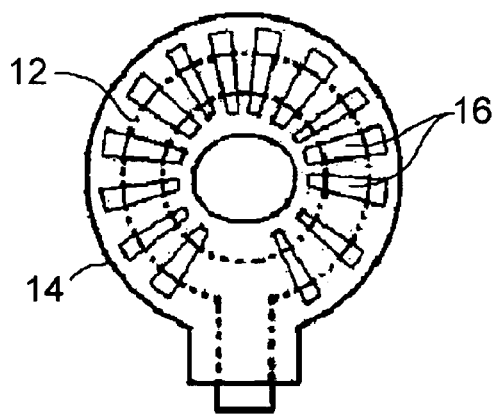
Figure 2:
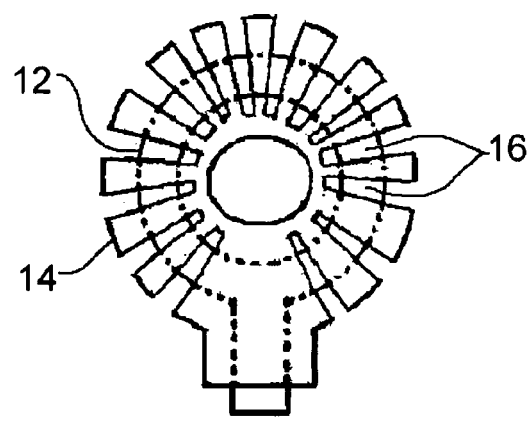

(a)
 (b)
 (c)
 (d)
 (e)
 (f)

BIOMEDICAL SURFACE ELECTRODE

This invention relates to a surface electrode which can be used medically to receive and transmit biosignals emanating from a body or to apply low level electrical signals to the body, herein referred to as a biomedical surface electrode.

Biomedical surface electrodes are well known. For example, one such electrode consists of a silver-plated eyelet which is housed within a recessed plastic element or cup. A snap fastener stud is located on the outside of the plastic element and acts as a means of connecting the external circuitry to the electrode. In this type of electrode there is a sponge which has been impregnated with an electrolytic gel and which is located within the plastic electrode housing so that when in use the sponge serves as a conductive bridge between the eyelet and the patient's skin. The electrolytic gel enhances the conductivity of the skin and ensures good electrical contact between the patient and the metal sensor. Since the electrode system must have good contact with the skin, the present technology provides that the plastic housing incorporating the eyelet sensor, with its conductive gel, be attached to a disc of open cell plastic foam or microporous tape, which is coated on its underside with a medical-grade contact adhesive. This resilient adhesive disc serves to attach the system to, and hold it on the patient's skin. Finally, for storage purposes a cap is placed over the rigid plastic element in order to isolate the electrode from the atmosphere and thus prevent the drying-out of the conductive gel, which is water based.

Electrodes of the above type have proved quite reliable in establishing an electrical connection to the patient, but associated with them are several disadvantages. Firstly the design incorporates many components which render the electrode somewhat complex in assembly and therefore relatively expensive to manufacture. Secondly it has a large profile, covers a considerable skin area and lacks flexibility. This rigidity of the element, or housing, can give rise to skin abrasion and irritation and pull on the connecting lead affects the sensor and can give rise to motion artefact signals.

Recently, simpler electrode designs have become available that employ a metal foil which acts as both an electrode sensor and as a means of connection to the external circuitry. The connection to the metal foil is via an exposed tab of foil which in general practice is grabbed by a small alligator clip. In this newer type a solid, adhesive, hydrogel serves both as the electrolyte and the adhesive means to the skin. The system has electrode flexibility, the desired low profile and it conforms well to body contours. Since the system dispenses with the conventional disc of adhesive backing, the overall electrode area is small. This electrode design is simple and less expensive to manufacture.

When current passes through a gelled biomedical surface electrode, the major portion of the current flows through the peripheral area of the electrode. For example, in high current situations, such as in external cardiac pacing and defibrillation via large surface electrodes, serious skin burns and pain can occur under the edges of the electrode due to the localised high current density "hot spots". Although it is not widely appreciated, a similar "edge" effect occurs in biosignal monitoring electrodes, albeit the current densities involved are much smaller and do not give rise to skin burns.

The present invention therefore seeks to provide a biomedical surface electrode having an improved current density distribution.

According to the present invention there is provided a biomedical surface electrode comprising a flexible electrically insulating substrate, a flexible electrically conductive electrode layer on the substrate, a flexible electrically insulating masking layer on the electrode layer, the masking layer being configured to expose selected regions of the electrode layer, and a flexible electrically conductive adhesive layer on the masking layer which makes electrical contact with the exposed regions of the electrode layer.

Embodiments of the invention will now be described, by way of example, with reference to the accompanying drawings, in which:

FIG. 1 is a cross-section through an embodiment of an electrode according to the invention.

FIGS. 2(a) to 2(f) are simplified plan views of the electrode of FIG. 1 showing various alternative configurations for the electrode and masking layers.

Referring to FIG. 1, a flexible biomedical surface electrode comprises an electrically insulating substrate 10 in the form of a heat stabilised, adhesion-treated clear polyester layer. The substrate 10 is used as the main structural body of the electrode to which all other components are assembled. The substrate is thin enough (typically 75 microns thick) to ensure flexibility. The substrate is coated on both sides with a treatment enabling an electrically conductive electrode layer 12 to adhere to it. An example of a suitable polyester layer for use as the substrate 10 is Mylar from Dupont. The electrode layer 12 is a flexible, conductive silver polymer ink which is screen printed onto the substrate 10. An example of a suitable ink is 5874 ink from Dupont.

A flexible electrically insulating masking layer 14 is screen printed onto the silver polymer ink electrode layer 12. However, as will be described with reference to FIG. 2, this layer 14 is configured to expose selected regions 16 of the electrode layer 12 where, in use, an electrical connection between the electrode layer 12 and a patient's skin is desired. For regions of the electrode layer which are not to come into contact with the skin the masking layer 14 acts as an insulator, forcing any current to flow only through the exposed regions 16 of the layer 12. An example of a suitable material for the masking layer 14 is SD 2460 Flex ink from Norcote.

A flexible electrically conductive adhesive hydrogel layer 18 is applied to the masking layer 14 which makes electrical contact with the exposed regions 16 of the electrode layer 12. The hydrogel layer 18 provides bio-compatible adhesion to the skin and a good skin-electrode interface. The hydrogel layer 18 is at least the same overall size and shape as the electrode layer 12 and ideally should overlap the perimeter of the latter. An example of a suitable hydrogel is FW340 hydrogel from Firstwater.

A flexible, electrically insulating foam layer 20 has a bio-compatible adhesive on one side for adhesion to the skin and to the substrate 10 whose non-printed side is adhered to the adhesive foam layer. The foam layer 20 extends beyond the perimeter of the substrate 10 by at least 5 mm. The adhesive perimeter region 22 ensures adhesive contact of the electrode assembly to the skin and protects the hydrogel during use. An example of a suitable foam material is 0.838 mm thick RX232V single sided PE foam from Scapa.

A rigid electrically conductive stud 24 comprising male and female parts 24A, 24B allows connection of the electrode layer 12 to the outside world. The stud 24 passes through the electrode, substrate and foam layers 10, 12 and 20 respectively and compresses these layers between the male and female parts. The stud 24 is a snap fastener type, for example, part no. 380335 from Prym fasteners.

The male part of the stud 24A has a flexible electrically insulating cover 26. This extends beyond the perimeter of the male part by a minimum of 2 mm thus avoiding the conductive stud from contacting the skin or the hydrogel. The stud cover can be an adhesive label which is waterproof, mark proof and resistant to UV, oil and grease. A material which could be used for this is a heavy duty laser label from Avery.

When not in use the electrode assembly is covered with a peelable flexible, electrically non-conductive release liner 28. A suitable material is PE140.01 single-sided silicon paper from Cotek.

The electrode is packaged in a foil laminate pouch (not shown) for maximum shelf life protection. A suitable material for the pouch is 35786-G from Perfecseal.

FIGS. 2(a) to 2(f) are plan views of the electrode of FIG. 1 showing various alternative configurations for the electrode and masking layers. It will be understood that only the electrode and masking layers 12 and 14 are shown in these figures.

The electrode layer 12 may be in the form of a solid figure, for example a disc, as shown in FIGS. 2(a) to 2(c). In FIG. 2(a) the masking layer 14 has a plurality of circular apertures distributed around the periphery of the electrode layer, exposing corresponding regions 16 of the electrode layer 12. There may be several concentric rows of circular apertures, FIG. 2(b), which can be the same size or vary in size to interfit and achieve a greater packing density. Other interfitting shapes such as star shapes, FIG. 2(c) may assist such packing.

Alternatively the electrode layer 12 may be in the form of a hollow figure, for example an annulus, as shown in FIGS. 2(d) to 2(f), with the masking layer 14 having a void at its centre corresponding to the central void in the annulus. In FIG. 2(d) the masking layer has a circular arrangement of apertures similar to FIG. 2(a), while FIG. 2(e) has apertures in the form of radial slots. The exposed regions 16 of the electrode layer 12 do not need to be defined by complete apertures in the masking layer. An example is shown in FIG. 2(f) which corresponds in electrical effect to FIG. 2(e) but wherein the slots extend beyond the perimeter of the electrode layer 12 fully to the perimeter of the masking layer 14, and are therefore open at their outer edges.

In all cases, however, the exposed regions 16 are preferably distributed at least around the perimeter of the electrode layer 12.

The patterned masking layer 14 serves to force the current through the layer 14 at predetermined locations, thus controlling the current density distribution. The circumference of the apertures or other patterning effectively gives rise to large peripheral edges to better disperse the current.

The exposed regions 16 are typically several mm across and a much larger number of them would be used than is shown in the drawings.

The invention is not limited to the embodiments described herein which may be modified or varied without departing from the scope of the invention.

The invention claimed is:

1. A biomedical surface electrode comprising a flexible electrically insulating substrate, a flexible electrically conductive electrode layer on the substrate, a flexible electrically insulating masking layer on the electrode layer, the masking layer being configured to expose selected regions of the electrode layer, and a flexible electrically conductive adhesive layer on the masking layer which makes electrical contact with the exposed regions of the electrode layer, the masking layer comprising a plurality of apertures which expose the selected regions of the electrode layer, wherein the apertures and exposed regions are distributed around the perimeter of the electrode layer and at least some of the apertures extend beyond the perimeter of the electrode layer, to force current to flow only through the exposed regions distributed around the perimeter of the electrode layer.

2. An electrode as claimed in claim 1, wherein the flexible electrically conductive adhesive layer comprises an adhesive gel layer.

3. An electrode as claimed in claim 2, wherein the electrode layer is in the form of a solid figure.

4. An electrode as claimed in claim 2, wherein the electrode layer is in the form of a hollow figure.

5. An electrode as claimed in claim 1, wherein the electrode layer is in the form of a solid figure.

6. An electrode as claimed in claim 5, wherein the electrode layer is in the form of a disc.

7. An electrode as claimed in claim 1, wherein the electrode layer is in the form of a hollow figure.

8. An electrode as claimed in claim 7, wherein the electrode layer is in the form of an annulus.

9. An electrode as claimed in claim 1, wherein the at least some of the apertures extend beyond the perimeter of the electrode layer fully to the perimeter of the masking layer and are open at their outer edges.

10. An electrode as claimed in claim 1, wherein the at least some of the apertures extending beyond the perimeter of the electrode layer comprise circular or star-shaped apertures.

11. An electrode as claimed in claim 1, wherein the at least some of the apertures extending beyond the perimeter of the electrode layer comprise apertures in the form of radial slots.

12. An electrode as claimed in claim 1, wherein the electrode layer comprises an electrode layer in the form of a hollow figure with a void at the center of the electrode layer.

13. An electrode as claimed in claim 12, wherein the at least some of the apertures extend beyond the perimeter of the electrode layer and beyond the perimeter of the void at the center of the electrode layer.

14. An electrode as claimed in claim 1, wherein the electrode layer comprises an electrode layer in the form of annulus.

* * * * *